(12) United States Patent
Axen et al.

(10) Patent No.: US 8,758,682 B2
(45) Date of Patent: Jun. 24, 2014

(54) METHOD AND DEVICE FOR SMALL SCALE REACTIONS

(75) Inventors: Andreas Axen, Uppsala (SE); Anders Larsson, Uppsala (SE); Nils Norrman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 583 days.

(21) Appl. No.: 12/443,072

(22) PCT Filed: Sep. 24, 2007

(86) PCT No.: PCT/SE2007/000839
§ 371 (c)(1),
(2), (4) Date: Mar. 26, 2009

(87) PCT Pub. No.: WO2008/039130
PCT Pub. Date: Apr. 3, 2008

(65) Prior Publication Data
US 2010/0035273 A1    Feb. 11, 2010

(30) Foreign Application Priority Data
Sep. 29, 2006 (SE) ..................................... 0602062

(51) Int. Cl.
*C12Q 1/68* (2006.01)

(52) U.S. Cl.
USPC ....................................................... 422/50

(58) Field of Classification Search
None
See application file for complete search history.

(56) References Cited

U.S. PATENT DOCUMENTS

| | | | |
|---|---|---|---|
| 6,306,273 B1 * | 10/2001 | Wainright et al. | 204/454 |
| 6,632,641 B1 | 10/2003 | Brennan et al. | |
| 7,439,014 B2 * | 10/2008 | Pamula et al. | 435/4 |
| 2002/0001544 A1 * | 1/2002 | Hess et al. | 422/100 |
| 2002/0106314 A1 * | 8/2002 | Pelrine et al. | 422/186 |
| 2002/0150683 A1 * | 10/2002 | Troian et al. | 427/256 |
| 2003/0040129 A1 | 2/2003 | Shah | |
| 2003/0142901 A1 * | 7/2003 | Lahann et al. | 385/18 |
| 2004/0018611 A1 * | 1/2004 | Ward et al. | 435/287.2 |
| 2004/0043507 A1 | 3/2004 | Song et al. | |
| 2004/0171055 A1 | 9/2004 | Brown | |
| 2005/0064465 A1 * | 3/2005 | Dettloff et al. | 435/6 |
| 2005/0072917 A1 * | 4/2005 | Becker | 250/288 |
| 2005/0136552 A1 * | 6/2005 | Buechler | 436/514 |
| 2005/0196746 A1 | 9/2005 | Xu et al. | |
| 2006/0024841 A1 * | 2/2006 | Yao et al. | 436/180 |
| 2006/0246475 A1 * | 11/2006 | Peterson et al. | 435/6 |
| 2007/0052781 A1 * | 3/2007 | Fraden et al. | 347/96 |
| 2007/0102362 A1 * | 5/2007 | Iida et al. | 210/656 |
| 2008/0213853 A1 * | 9/2008 | Garcia et al. | 435/173.1 |
| 2011/0118136 A1 * | 5/2011 | Koster et al. | 506/9 |
| 2011/0151569 A1 * | 6/2011 | Rowell et al. | 436/86 |
| 2012/0295290 A1 * | 11/2012 | Campbell et al. | 435/7.94 |

FOREIGN PATENT DOCUMENTS

| | | |
|---|---|---|
| EP | 1 077 771 | 8/2007 |
| WO | WO 94/11421 | 5/1994 |
| WO | WO 99/57318 | 11/1999 |
| WO | WO 99/58245 | 11/1999 |
| WO | WO 03/072227 | 9/2003 |
| WO | WO 2006/112771 | 10/2006 |
| WO | WO 2007/094739 | 8/2007 |

OTHER PUBLICATIONS

Xia, Y., et al., "Surface patterning and its application in wetting/dewetting studies", Current Opinion in Colloid and Interface Science, 6 (2001) 54-64.

"Hydrophobic Surfaces" The Kendall Award Symposium Honoring Albert C. Zettlemoyer Division of Colloid and Surface Chemistry at the 155th Meeting of the American Chemical Society San Francisco, CA, Apr. 1-2, 1968, edited by Frederick M. Fowkes (1969) Academic Press, New York and London.

Andersson, P. E., "Enhanced Protein Identification Using Microfluidic Technology" PharmaGenomics, 2 (2003) 38-44.

* cited by examiner

*Primary Examiner* — Ann Lam

(57) ABSTRACT

The present invention relates to a method and a device for small scale reactions, such as sample preparation of a desired substance in a sample. In the method using the device samples mixed with functionalized magnetic particles are magnetically transferred between different working stations on the device. The method uses a hydrophobic surface, such as a Petri dish, provided with hydrophilic spots of, for example, agarose beads located on said hydrophobic surface and provided with buffers, reactants or ligands.

12 Claims, 2 Drawing Sheets

METHOD AND DEVICE FOR SMALL SCALE REACTIONS

CROSS-REFERENCE TO RELATED APPLICATIONS

This application is a filing under 35 U.S.C. §371 and claims priority to international patent application number PCT/SE2007/000839 filed Sep. 24, 2007, published on Apr. 3, 2008, as WO 2008/039130, which claims priority to patent application number 0602062-2 filed in Sweden on Sep. 29, 2006.

FIELD OF THE INVENTION

The present invention relates to a method and a device for small scale reactions, such as sample preparation of a desired component in a sample. In the method using the device samples mixed with magnetic particles are transferred between different working stations on the device.

BACKGROUND OF THE INVENTION

There are many sample preparation methods used today. For example, electrophoresis is a widely used method for sample preparation of proteins and peptides. The sample may be separated in 1 dimensional or 2 dimensional electrophoresis, wherein 1D electrophoresis separates molecules on the basis of e.g. pI-value and 2D electrophoresis includes an additional separation according to size and possibly charge. For sample preparation, electrophoresis is cumbersome and time consuming. Another drawback is that the sample has to be eluted from the gel if it is desired to use or analyse the sample further.

Another example of sample preparation is liquid chromatography which may be used as 1D, 2D or MDLC (multi dimensional liquid chromatography) separation. The liquid chromatography may be sieving chromatography, ion exchange chromatography, hydrophobic interaction chromatography, affinity chromatography etc. The drawback with liquid chromatography is that it is less suited for handling very small amounts of sample. The limitation in handling small amounts of sample with chromatographic methods is in part overcome by using so called micro spin columns.

Other techniques that are currently in use for sample preparation of very small sample amounts make use of pre-coated microtiter plates. These plates can be prepared with ligands that can remove bulk impurities as well as be used for specific isolation of target components.

Yet another sample preparation approach is based on the use of magnetic beads. Magnetic beads are also available with ligands suited for removal of bulk proteins or isolation of specific target components. These materials are commonly handled in test tubes in combination with a manual pipetting procedure.

Various types of microfluidic systems have also been described for sample preparation and other manipulations (see e.g. P E Andersson: PharmaGenomics (2), 38-44 (2003)). A drawback in many of these is that the macro/micro interface becomes inconvenient, i.e. the transfer of a macroscopic (microliter/milliliter) sample into channels of nano/picoliter dimensions is a weak spot in the system. Further, they are often not well suited for handling small amounts of particulate materials.

SUMMARY OF THE INVENTION

The present invention provides a system or device for small scale reactions of samples, wherein magnetic particles adhering/binding to specific compounds in the sample are transferred between different working stations or spots located on the device. In this way a desired component of the sample may be for example separated from the remainder of the sample and/or impurities may be removed from a target component. The invention also has broader implications on sample manipulation in general. It may be applied wherever small amounts of magnetic particles with bound/adhering substances need to be moved, divided, separated, mixed, washed or reacted with different solutions.

Thus, the present invention relates to a convenient procedure for the transfer of small amounts of magnetic beads or particles between different stations based on the use of functionalised magnetic particles, a hydrophilic/hydrophobic patterned surface, and one or more magnet(s)/magnetic field(s).

In a first aspect, the invention relates to a device or system comprising a hydrophobic surface provided with hydrophilic spots located on said hydrophobic surface; functionalised magnetic particles; and means to be provided beneath or above the hydrophobic surface for transferring the magnetic particles between the hydrophilic spots. The hydrophobic surface of the device is preferably a substantially planar surface, such as a polymer film, a Petri dish, a planar slide, a microfabricated device. Alternatively, the device is a multi-well plate.

The hydrophilic spots may be present in a desired number depending on the desired number of reactions. The hydrophilic spots are preferably made of polysaccharide beads, such as agarose beads, oxidized polymer, metal, inorganic oxide, glass, ceramic, hydrophilic polymer, hydrophilic silane, hydrophilic thiols. The spots may be provided with buffer, detergent, reactant or ligand(s), or any combination thereof. In one embodiment the spot content is in a dry state before use.

The sample may also already be provided at the first spot before the magnetic particles are added thereto.

If affinity ligands are provided in the spots they may be antibodies, fractions of antibodies, proteinaceous structures, aptamers, peptides, synthetic organic molecules, lectins, carbohydrates or metal chelating ligands, or any combination thereof.

The magnetic beads or particles may be functionalised with affinity ligands, metal chelating ligands, ion exchange ligands, hydrophobic ligands and/or reactive groups. Depending on the application the magnetic beads or particles may be made biocompatible, i.e. provided with biocompatible outer layer(s) preventing metal leakage, for example as described in WO 06/112771. The affinity ligands on the magnetic beads may for example be antibodies, fractions of antibodies, proteinaceous structures, aptamers, peptides, synthetic organic molecules, lectins, carbohydrates or metal chelating ligands or lectins, or any combination thereof.

The means to be provided beneath or above the hydrophobic surface is a handheld magnet or an automatically directed magnet or a magnetic field produced by one or more electromagnet coils.

In one embodiment the hydrophobic surface with the hydrophilic spots is a closed system, closed for example with a lid.

In a further embodiment, the device is a microfluidic device with hydrophobic top and bottom portions each provided with hydrophilic spots, and an inlet/outlet port for sample. A pattern of channels may be provided between the top and bottom portion for control of fluid movement.

In a second aspect, the invention relates to a method for performing small scale reactions, comprising the following steps: (a) adding functionalised magnetic particles to a sample to perform a first reaction on a first hydrophilic spot provided with buffers(s), reactant(s) and/or ligand(s), wherein the hydrophilic spot is located on a hydrophobic surface and wherein the magnetic particles are functionalised to bind/adhere to at least one target compound in the sample, and (b) magnetically transferring said magnetic particles with or without bound target to a second hydrophilic spot on said hydrophobic surface for a further reaction of the sample, wherein said second hydrophilic spot is provided with buffers (s), reactant(s) and/or ligand(s).

The sample may be mixed with magnetic beads and then the mixture may be provided on the first spot, or the sample may already be provided on the first spot when the magnetic beads are added.

The target compound may be positively selected from said sample. Alternatively, the target compound is depleted from said sample. In another embodiment the sample is subjected to a combination of one or more positive and negative selection steps.

In yet another embodiment the target compound is synthesized by reactions on the hydrophilic spots, for example a peptide or oligonucleotide may be synthesized.

In a third aspect, the invention relates to use of the device according to the invention for small scale reactions of any biomolecule such as cells, cellular components, proteins, peptides, nucleic acids, lipids and carbohydrates.

In a preferred embodiment, the small scale separation is sample preparation of cells, proteins, peptides or nucleic acids.

The device of the invention may also be used for synthesis of peptides or nucleic acids as well as for sequencing of nucleic acids.

DEFINITIONS

Figure 1:
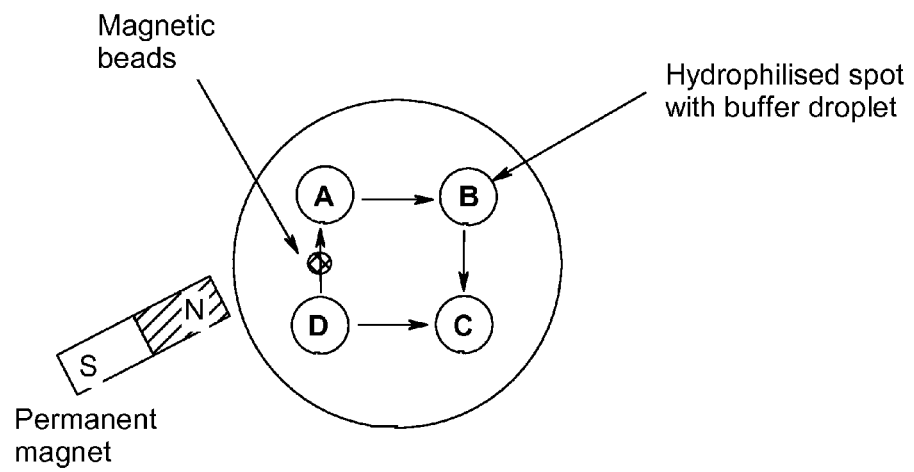
FIG. 1 shows a schematic example of the device of the invention comprising a polystyrene surface with hydrophilized spots or stations with buffer droplets.

Station or spot: a hydrophilized location on a hydrophobic device according to the invention.

Hydrophilized: means any way to achieve hydrophilization, such as plasma treatment, covalent coupling or the method described in WO 9411421.

Ligand: means any ligand, such as an affinity ligand, for example antibody, fragment of antibody, aptamer, peptide ligand.

The terms hydrophobic and hydrophilic are well known to those skilled in the art, but they can be defined in different ways. In the present context, a hydrophobic surface is poorly wetted by water, i.e. a water drop does not spread but stands up in the form of droplets with an easily measured contact angle. The contact angle is measured with a goniometer from the plane of the surface, tangent to the water surface at the three phase boundary line. Thus, hydrophobic surfaces have been characterized as having high contact angles with water, often in the range of 40-50 degrees and upwards (A C Zettlemoyer, Hydrophobic Surfaces, Ed. F. M. Fowkes, Academic Press 1969, (New York). Hydrophilic surfaces on the other hand have low contact angles with water, typically from 0 to 40 degrees. Examples of materials with intrinsically hydrophobic surfaces include hydrocarbon polymers, halogenated hydrocarbon polymers, many ester polymers etc, whilst intrinsically hydrophilic materials include non-contaminated metals or metal oxides, other ceramics, glasses and polysaccharides etc. It should also be noted that both hydrophobic and hydrophilic materials can be modified to change their surface characteristics dramatically.

To create a pattern of hydrophilic areas surrounded by a hydrophobic area, there are three basic principles that can be utilized:
a) A hydrophobic substrate is selectively modified to create hydrophilic spots.
b) A hydrophilic substrate is selectively modified to become hydrophobic everywhere except in the areas designed to remain hydrophilic.
c) A substrate is modified twice to become hydrophilic in certain areas and hydrophobic in the remaining areas (or vice versa).

In method a), the substrate is often a hydrophobic plastic that is made hydrophilic in designed areas. The hydrophilization techniques may be e.g. irradiation with UV light, electron beams, ion beams etc, treatment with a glow discharge plasma, barrier discharge or corona discharge, graft polymerization with hydrophilic monomers (including photoinitiated grafting), deposition (printing, ink-jet application, spraying, writing etc.) of hydrophilic polymers, photo/EB-polymerization of deposited hydrophilic monomers/macromonomers, reaction with oxidizing etchant solutions or other methods. To protect the designated hydrophobic areas from modification, any irradiation may be done through a stencil mask, the surface may be protected from discharges or etchants with a masking film applied in a pattern, or hydrophilic polymers may be deposited specifically in designated areas only. An example is the method described in WO 9411421. It describes a method of modifying a polymer based surface with (hydrophilic) particles comprising converting the top layer of the polymer based surface to a swollen or semi swollen state without the use of adhesive and simultaneously or subsequently contacting the polymer based surface with the particles.

Method b) is typically used with glass, ceramics, metals etc. A hydrophobic pattern is applied in designated areas by contact printing, inkjet application, spraying, writing etc, using a hydrophobic film-forming material (e.g. a polymer solution/dispersion, a hydrophobic silane, a hydrophobic thiol etc.). Alternatively, the surface may be made hydrophobic everywhere except in areas protected by a stencil mask or a contact masking film, using plasma polymerization of hydrophobic monomers, graft polymerization of hydrophobic monomers (including photografting), photo/EB-polymerization of deposited hydrophobic monomers/macromonomers, dip/spray coating with hydrophobic polymers/silanes/thiols etc.

In method c), any of the a) and b) techniques may be used in combination.

DETAILED DESCRIPTION OF THE INVENTION

The method is based on the creation of a surface pattern with well defined hydrophilic and hydrophobic regions, e.g. as described in numerous publications. Some examples are given in EP1077771A1 and Y Xia et al: Curr Opin Coll Interf Sci 6,54-64 (2001) or by surface modification of a poly styrene surface using a known procedure based on the spot wise attachment of agarose beads to the surface by a gluing method as described in WO 9411421. This modification allows for an improved control of small aliquots of any aqueous liquid put on these spots as droplets as buffer stations. The hydrophilic spots may be provided with beads or particles which may or may not be provided with ligands. The hydrophilic spots may also be provided with buffers or other reagents.

Functionalised magnetic beads can thereafter be transferred from different "stations" on the substrate surface by simply dragging the beads with a hand held permanent magnet from the back side of the polystyrene surface. The method used for hydrophilisation of the substrate surface results in a remarkable low transfer of buffer liquid from one station to the other.

The device can be an open construction, where buffer/reagent droplets are placed at the different hydrophilic stations on a single patterned substrate surface using pipettes, dispensing robots etc. It can also be closed, with a lid over the substrate. In this case it may be advantageous to have hydrophilic areas on the lid surface at locations corresponding to the hydrophilic stations on the substrate surface. In this case the droplets may be introduced through a number of inlet ports (openings in the lid or from the edge of the device) and directed to the stations by capillary suction, centrifugation, locally applied vacuum/pressure etc. It may also be possible to apply dry films of buffer/reagent components at specific stations by e.g. printing or inkjet application and to reconstitute the solutions with water immediately before use of the device. In addition to the hydrophilic station pattern, the device may also have a pattern of channels for control of fluid movements.

Examples of applications of the device of the invention include purification of components (magnetic particle population moved to droplet of sample solution, specific target species adsorb, particles moved to eluent droplet, specific target species desorb etc), detection of components (magnetic particles with adhering target species moved to detection station), synthesis of components or substances (magnetic particles moved to first reagent droplet and then, via washing droplets, sequentially through a series or different reagent droplets) etc.

More specifically a station can contain a droplet of sample liquid and magnetic beads carrying a ligand directed towards a specific target compound are added. After incubation the magnetic beads are transferred to a new station consisting of a small aliquot of washing buffer. The washing step may be repeated by transferring to further washing stations with the same or other washing buffers. Thereafter the magnetic beads now carrying the separated target compound are transferred to a station with elution buffer, e.g. a buffer possessing high ionic strength, high or low pH, or other specific elution conditions. After incubation the liquid at this station will contain the target compound and the magnetic beads can be removed and the liquid containing the target compound is collected.

In another embodiment the magnetic beads are possessing ligands directed towards one or more of bulk contaminating substances. In this case the beads are incubated at the starting station with the sample and are there after removed leaving the partially purified target compound at the starting station.

In yet another embodiment the hydrophilized spots, for example agarose beads, at the various stations are derivatised with ligands that remove specific impurities. E.g. the magnetic beads carry ligands that have a broad affinity, i.e. the potential to interact with several compounds in the sample liquid, while the first station is constructed with agarose beads that specifically remove one contaminating compound. By moving the magnetic beads to the next station all sample compounds except the specific contaminating compound that was bound at the starting station are transferred. The second station can then consist of agarose beads that carry another specific ligand that removes yet another contaminating compound. By performing this procedure contaminating compound can be removed in a sequential fashion.

In a detection embodiment, the magnetic particles may be transferred to a sample droplet at a first station where the analyte binds to the particles. (This step may be repeated with several sets of magnetic particles binding different analytes) Then they can be transferred via one or several washing stations to one or more detection station(s). Examples of detection methods used in this station are: optical assessment of aggregation (e.g. after addition of immunological reagents such as antibodies or antigens), absorbance measurement (e.g. after addition of enzyme-conjugated antibodies and a chromogenic enzyme substrate), fluorescence (e.g. after addition of fluorescence-labelled reagents), mass spectrometry, radiochemical detection etc. For certain detection methods it may be advantageous to detach the analyte from the beads at the detection station and then remove the beads by a magnet before detection. For certain analytes it can be advantageous to perform an amplification step at a station before detection, e.g. through PCR reaction for nucleic acid samples.

In a synthesis embodiment, the magnetic particles are reacted with a first reagent at one station, passed through one or more washing stations and then to a next synthesis station where they are reacted with another reagent, continuing in a consecutive way until a sufficient number of reactions have been performed. Examples of reactions include solid phase peptide or oligonucleotide synthesis according to known methods, combinatorial chemical synthesis, block copolymer synthesis by living polymerization techniques etc. For parallel synthesis of combinatorial libraries, the particle population may be split into several aliquots after any given step and it is also possible to combine two or more particle populations before a synthesis step. Splitting of a particle population may be performed e.g. by having embossed recesses in the substrate surface, where a specific amount of particles can be trapped and later moved to another station by a magnet. Mixing of two populations may be achieved e.g. by moving a first population into a droplet at a station, removing the magnetic field (by shutting off an electromagnet or by removing a permanent magnet perpendicularly to the substrate) and then moving a second population into the same droplet. Alternatively, various embossed/microfabricated recess constructions may be used for mixing.

EXAMPLES

The present invention will be described in more detail by way of examples, which however are in no way intended to limit the scope of the present invention as defined by the appended claims. All references given below or elsewhere in the present specification are hereby included herein by reference.

Example 1

Positive Selection of Protein in Sample

50 µL of a 30% slurry of magnetic agarose beads, see for example WO 06/112771, functionalised with a metal chelating ligand charged with nickel is contacted with a 50 µL sample containing a His-tagged protein at station A. Thereafter the magnetic beads are consecutively dragged to station B and C containing 100 µL neutral buffers in order to wash away non specifically adsorbed proteins, followed by transfer to stations D possessing 100 µL of imidazole containing buffer that releases the target protein. The magnetic beads can thereafter be removed by dragging them away with the magnet, leaving a droplet containing isolated target protein at station D. (FIG. 1)

Example 2

Depletion of Contaminating Protein in Sample

50 μL of a 30% slurry of magnetic agarose beads functionalised with a serum albumin binding protein are 1) contacted with a 100 μL sample containing proteins where a bulk contaminant is serum proteins. Thereafter the magnetic beads are dragged to station B. Thereafter the sample at the starting station can be used in analytical experiments, or 2) 50 μL of further magnetic bead slurry may be added with another ligand directed towards another contaminating protein followed by transfer of these magnetic beads to station C, leaving the sample at the starting station now depleted from to major contaminating fractions.

Figure 2:
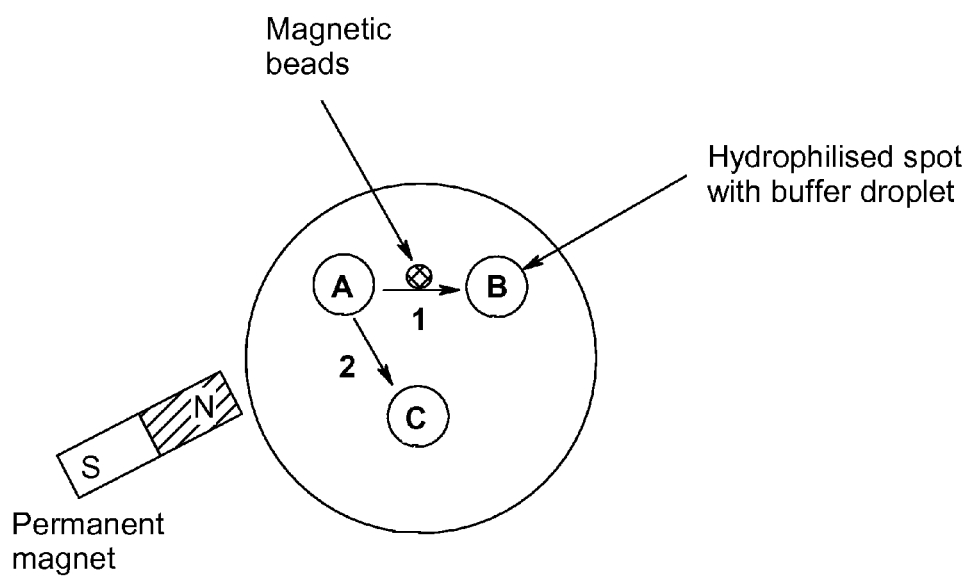
FIG. 2 shows another schematic embodiment of the device of the invention.

This procedure can be repeated as many times as desired with magnetic beads possessing different specific or group specific ligands. (FIG. 2)

Example 3

Sequential Negative Depletion

Figure 3:
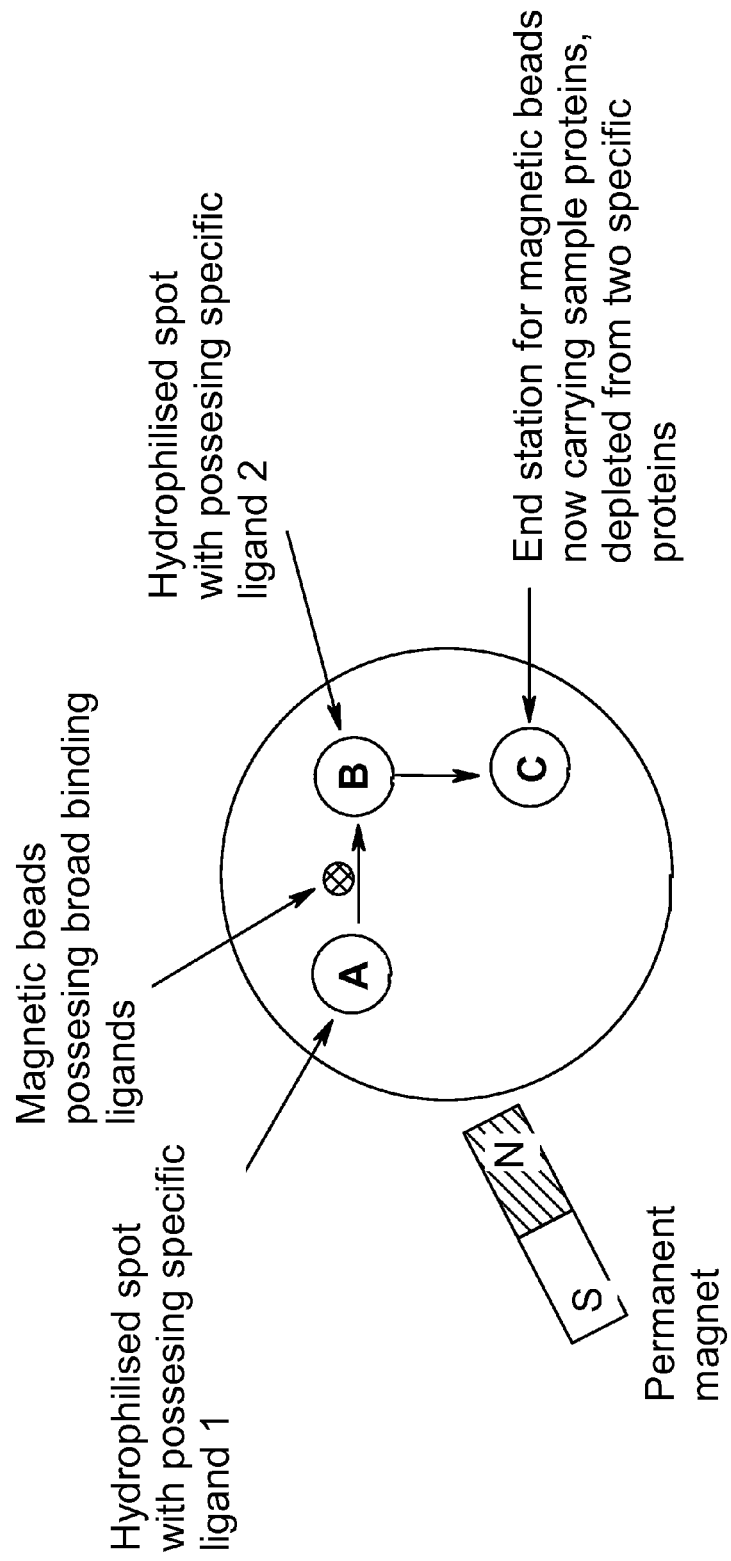
FIG. 3 shows a further schematic embodiment of the device of the invention.

A simple example on how this could be used in practice for negative selection with pre-activated stations is described in FIG. 3. 100 μL of a sample is applied to the starting station consisting of agarose beads possessing Protein A that specifically binds immunoglobulins in the sample. The sample is applied in a buffer with high pH so that the bulk of the proteins will have a negative charge. Thereafter 50 μL of a 30% slurry of magnetic agarose beads functionalised with an anion exchanging ligand binding the negatively charged proteins, except the immunoglobulins that are withheld by the Protein A ligands on the agarose beads. Thereafter the magnetic beads are dragged to station B. At station B the sample can be used in analytical experiments, now depleted from immunoglobulins, or 2) the agarose beads at station B are equipped with another specific ligand that under the same or altered buffer conditions specifically depletes yet another fraction from the sample. In this latter case the sample can be transferred to new stations using the same or other magnetic beads.

This procedure can be repeated as many times as desired with stations possessing different ligands and magnetic beads possessing different ligands. (FIG. 3)

Example 4

Positive Selection of Cells in Sample

50 μL of a 30% slurry of magnetic agarose beads functionalised with a CD4 binding ligand is contacted with a 50 μL sample containing a cell mixture including CD4 positive cells. Thereafter the magnetic beads are consecutively dragged to station B and C containing 100 μL neutral buffers in order to wash away non specifically adsorbed cells, followed by transfer to stations D possessing 100 μL of excess of a monoclonal antibody directed towards CD4 competing with the interaction of the magnetic beads and the cells and hereby releases the target cells. The magnetic beads can thereafter be removed by dragging them away with the magnet, leaving a droplet containing isolated target cells at station D.

Example 5

Negative Depletion of Contaminating Cells in Sample

50 μL of a 30% slurry of magnetic agarose beads functionalised with a CD4 binding ligand are 1) contacted with a 100 μL sample containing CD4 positive cells in a mixture. Thereafter the magnetic beads are dragged to station B. Thereafter the sample at the starting station can be used in analytical experiments, or 2) 50 μL of further magnetic bead slurry may be added possessing another ligand directed towards another cell surface protein of a contaminating cell line followed by transfer of these magnetic beads to station C, leaving the sample at the starting station now depleted from to major contaminating cell fractions.

This procedure can be repeated as many times as desired with magnetic beads possessing different specific or group specific ligands directed towards cell surface proteins.

The above examples illustrate specific aspects of the present invention and are not intended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A device comprising a hydrophobic surface provided with hydrophilic spots located on said hydrophobic surface; functionalised magnetic particles; and means beneath or above the hydrophobic surface for magnetically transferring the magnetic particles between the hydrophilic spots; wherein there is hydrophobic surface between the hydrophilic spots.

2. The device of claim 1, wherein the hydrophobic surface is a substantially planar surface.

3. The device of claim 1, wherein the hydrophilic spots are made of polysaccharide beads, oxidized polymer, metal, inorganic oxide, glass, ceramic, hydrophilic polymer, hydrophilic silane or hydrophilic thiols.

4. The device of claim 1, wherein the spots are provided with buffer(s), reactant(s), and/or ligand(s).

5. The device of claim 4, wherein the spot content is in a dry state before use.

6. The device of claim 1, wherein the magnetic particles are functionalised with affinity ligands, metal chelating ligands, ion exchange ligands, hydrophobic ligands, or reactive groups.

7. The device of claim 4, wherein the affinity ligands provided in the spots are antibodies, fractions of antibodies, proteinaceous structures, aptamers, peptides, synthetic organic molecules, lectins, carbohydrates or metal chelating ligands, or any combination thereof.

8. The device of claim 6, wherein the affinity ligands provided on the magnetic beads are antibodies, fractions of antibodies, proteinaceous structures, aptamers, peptides, synthetic organic molecules, lectins, carbohydrates or metal chelating ligands, or any combination thereof.

9. The device of claim 1, wherein the means beneath or above the hydrophobic surface is a handheld magnet or an automatically directed magnet or a magnetic field produced by one or more electromagnet coils.

10. The device of claim 1, wherein the hydrophobic surface with the hydrophilic spots is a closed system.

11. The device of claim 10, which is a microfluidic device provided with hydrophobic top and bottom portions each provided with hydrophilic spots at corresponding locations, and an inlet/outlet port for sample.

12. The device of claim 11, wherein a pattern of channels are provided between the top and bottom portion for control of fluid movement.

\* \* \* \* \*